US000001337H

United States Statutory Invention Registration [19]

[11] Reg. Number: H1337

Hoeppel

[43] Published: Jul. 5, 1994

[54] PROCESS FOR BIODEGRADATIOON OF SOIL CONTAMINANTS THAT CONTAIN VOLATILE/SEMIVOLATILE COMPONENTS

[75] Inventor: Ronald E. Hoeppel, Oak View, Calif.

[73] Assignee: The United States of America as represented by the Secretary of the Navy, Washington, D.C.

[21] Appl. No.: 948,036

[22] Filed: Sep. 21, 1992

[51] Int. Cl.[5] ..... C12M 1/04; C12M 1/06

[52] U.S. Cl. ..... 435/313; 435/262.5

[58] Field of Search ..... 435/3, 262, 262.5, 266, 435/284, 291, 299, 300, 311, 313, 315; 55/74, 98, 233, 387, 418, 419; 210/612, 613, 615, 617, 150, 151; 405/128, 129

[56] References Cited

U.S. PATENT DOCUMENTS

| | | | |
|---|---|---|---|
| 4,662,900 | 5/1987 | Ottengraf | 435/262 |
| 4,962,034 | 10/1990 | Khan | 435/262 |
| 5,017,289 | 5/1991 | Ely et al. | 210/610 |
| 5,057,227 | 10/1991 | Cohen | 210/680 |
| 5,059,252 | 10/1991 | Renfro | 435/281 |
| 5,080,782 | 1/1992 | Caplan et al. | 210/151 |
| 5,120,160 | 6/1992 | Schwengel | 405/128 |

OTHER PUBLICATIONS

Leson et al., "Biofiltration: An Innovative Air Pollution Control Technology for VOC Emissions", J. Air Waste Manage. Ass., vol. 41, (Aug. 1991), pp. 1045–1053.

R. E. Hoeppel, "Biodegradation for On-Site Remediation of Contaminated Soils and Groundwater at Navy Sites", Military Engineer, Aug. 1989, vol. 81; pp. 31–36.

*Primary Examiner*—Robert L. Stoll
*Assistant Examiner*—Joseph D. Anthony
*Attorney, Agent, or Firm*—Melvin J. Sliwka; David S. Kalmbaugh

[57] ABSTRACT

A biodegradation apparatus comprising an enclosed vessel for holding a large volume of soil contaminated with hydrocarbons. Air diffusers uniformly within the vessel force moistened air through the vessel thereby removing volatile hydrocarbons from the contaminated soil. Outgoing air is supplied to vapor phase bioreactor for the removal of hydrocarbon contaminants from outgoing air. The outgoing air is next supplied to a granular activated carbon filter system which absorbs remaining hydrocarbons and then expels non-polluted air into the atmosphere concluding phase one treatment of the hydrocarbon contaminated soil. Phase two treatment of the hydrocarbon contaminated soil is initiated by utilizing high pressure injection nozzles to force water with surfactant additives through the soil thereby forming at the upper portion of the enclosed vessel a supernatant which includes hydrocarbon contaminants. The supernatant is next provided to a settling tank that collects oily sludge at the bottom thereof and then to a treatment tank where nutrients are added to promote biological growth for biodegradation of the remaining hydrocarbon contaminants.

15 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR BIODEGRADATIOON OF SOIL CONTAMINANTS THAT CONTAIN VOLATILE/SEMIVOLATILE COMPONENTS

BACKGROUND OF THE INVENTION

1. Field of the Invention

The present invention relates generally to biodegrading contaminated soils and, in particular, to a method and apparatus for the removal of volatile hydrocarbons and the like from contaminated soils.

2. Description of the Prior Art

Recent environmental legislation such as the Comprehensive Environmental Response, Compensation and Liability Act of 1980 and the Superfund Amendments and Reauthorization Act of 1986 have identified certain hazardous waste sites as requiring cleanup utilizing treatment technologies that will permanently and significantly reduce the volume, toxicity, or mobility of hazardous substances at these waste sites. This legislation further directs that permanent remedies be chosen for the cleanup of these hazardous waste sites and that offsite disposal of contaminants should be the least favored alternative for disposal of hazardous waste.

In complying with this environmental legislation the military has identified a significant number of their facilities as being hazardous waste sites requiring cleanup. Typically, the soils at these sites are contaminated with highly volatile hydrocarbon compounds such as gasolines and chlorinated solvents as well as hydrocarbon compounds having moderate to low volatility such as jet fuel, diesel fuel, engine oil and lubricants.

These hazardous waste sites also have underground storage tanks which are regulated by this environmental legislation and which are being used to store diesel fuel, gasoline and jet fuels. A significant portion of these underground storage tanks are over twenty years old or are fabricated from concrete which is permeable to most organic liquids. Thus, there is a high probability, with some estimates exceeding fifty percent, that these underground storage tanks are leaking and thus contaminating the soils surrounding the underground storage tanks.

Biodegradation has long been recognized as a process for the removal of toxic chemicals from the environment. In the past, for example, wastewater treatment plants have used biological processes to remove toxic chemicals and other contaminants from wastewater.

Bioremediation, which is the controlled use of biodegradation to remove toxic contaminants from soil, water and the like has also been used to remove petroleum hydrocarbons from contaminated surface soils and water. Bioremediation generally relies on the hydrocarbon degrading abilities of biological materials such as bacteria, fungi, bacterial enzymes, or fungal enzymes to degrade hydrocarbon contaminated soil. The hydrocarbon degrading biological materials are often naturally present in contaminated soil and given sufficient time can naturally degrade the hydrocarbon contaminants. In addition, this natural degradation process can often be promoted by directly adding biological materials such as hydrocarbon degrading microorganisms to soil in an amount sufficient to degrade the hydrocarbon contaminants or by encouraging the proliferation of hydrocarbon degrading organisms either naturally present in soil or present as a result of inoculation.

Bioremediation of hydrocarbon contaminated soils is favored over soil removal or chemical treatment of soil because of lower cost, proven effectiveness and ability for reduction of hydrocarbon contamination. While satisfactory for their intended purpose of removing contaminants such as hydrocarbons from soil, prior art bioremediation processes ordinarily leave something to be desired in that even under optimum conditions, months or years may be required to decrease the levels of hydrocarbon contamination to the desired levels. This disadvantage has greatly limited the potential use of bioremediation to reduce hydrocarbon contamination in soils.

It is therefore an object of this invention to provide an apparatus and method for accelerated biodegradation of hazardous organic substances in soils.

It is a further object of the present invention to significantly reduce the levels of hydrocarbon contamination of soils within a relatively short period of time after arrival at the hazardous substance contaminated site.

It is yet a further object of the present invention to provide a method and apparatus which permits continual, effective and highly efficient treatment of hydrocarbon contaminated soils.

Various other objects and advantages of the present invention will become more apparent to those skilled in the art as a more detailed description of the invention is set forth below.

SUMMARY OF THE INVENTION

The above and other objects of the present invention are accomplished by a biodegradation apparatus comprising an enclosed primary vessel that is impermeable to liquids and which is capable of holding a large volume of soil contaminated with hydrocarbons such as gasoline, oil, chlorinated solvents and the like. Air diffusers uniformly positioned at the bottom of the vessel force moistened air through the vessel thereby removing volatile hydrocarbons from the contaminated soil at an accelerated rate. Outgoing air from the vessel is provided to a vapor phase bioreactor for the removal of volatilized hydrocarbon contaminants in the outgoing air. The outgoing air is next supplied to a granular activated carbon filter system which absorbs remaining hydrocarbons and then expels non-polluted air into the atmosphere. This extraction of volatile hydrocarbon vapors from the soil constitutes the first phase of the biodegradation process implemented by the present invention.

Phase two treatment of the hydrocarbon contaminated soils is initiated by utilizing high pressure injection nozzles to force water with surfactant additives through the soil thereby forming a fluidized soil suspension in the lower portion of the enclosed vessel and at the upper portion of the enclosed vessel a supernatant layer which includes hydrocarbon contaminants. The hydrocarbon contaminants in the supernatant may be an oily film or emulsion, or may be attached to fine suspended clay sized particles The supernatant is next provided to a settling tank that collects oily sludge and particulates at the bottom thereof and then to a treatment tank where commercially available nutrients are added to promote biological growth whereby the remaining hydrocarbon contaminants can be converted by biodegradation into nontoxic by-products. When the water in the second treatment tank is rendered nontoxic thereby being in an environmentally-safe condition, the water is again reinjected with or without an emulsifying agent into the enclosed primary vessel for treatment of contaminated soils within the vessel.

DETAILED DESCRIPTION OF THE PREFERRED EMBODIMENT

Figure 1:
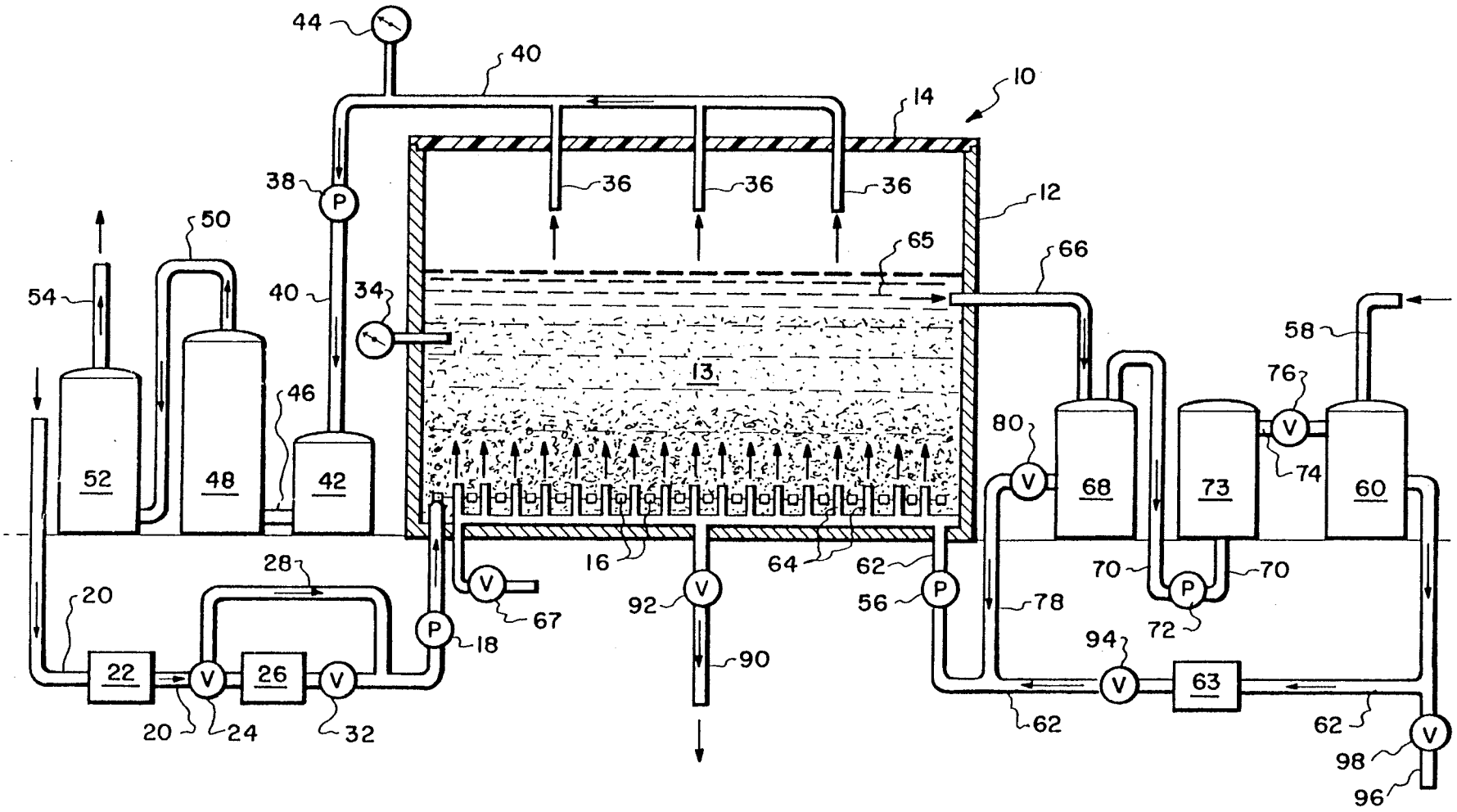
FIG. 1 is a schematic drawing of biodegradation apparatus constituting the present invention

Referring to FIG. 1, there is shown a biodegradation apparatus, designated generally by the reference numeral 10, which may be used to remove hydrocarbon contaminants such as gasoline, diesel, jet fuel, number six fuel oil, lubricant oil, crude oil, or the like from soils. Biodegradation apparatus 10 comprises an above ground holding vessel or tank 12 which may be fabricated from concrete or other nonporous materials sufficient in strength to hold a large volume of contaminated soil and water mixture 13. Vessel 12 has a removable top 14 which may be fabricated from a light weight, high strength plastic and which allows for the placement of contaminated soil 13 within vessel 12. Upon placement of the contaminated soil 13 within vessel 12, removable top 14 is sealed by conventional means such as a sealing tape such is air tight, thus being capable of supporting a low negative internal atmospheric pressure.

There is positioned at the bottom portion of vessel 12 a plurality of evenly spaced air diffusers 16 which forces moistened or dry air through the contaminated soil 13. The spacing of the air diffusers 16 within vessel 12, in turn, provides for a uniform distribution of air flow through the contaminated soil 13. A pump 18 draws air from the atmosphere via a pipe 20 through a heater 22 which heats the air to a temperature of 70° F.–90° F., if required, to a manually operated diverter valve 24. When the contaminated soil 13 in vessel 12 is saturated with water, diverter valve 24 is used to bypass a humidifier 26 by diverting air through a bypass pipe 28 to air diffusers 16. The heated air is then forced through the contaminated soil 13 at a pressure of approximately 30 psi by pump 18 drying the soil and removing from the soil volatile hydrocarbon vapors. It should be noted that a check valve 32 is positioned between the outlet port of humidifier 26 and the junction of pipe 20 and bypass pipe 28. Check valve 32, in turn, maintains the direction of flow of dry air from heater 22 through bypass pipe 28 to air diffusers 16.

When the contaminated soil 13 within vessel 12 is dry, that is moisture within the soil is less then 5%–6% by weight, diverter valve 24 may be set so that pump 18 draws air from the atmosphere through humidifier 26, which moistens the air to air diffuser 16. Pump 18 then forces the moisten air through the contaminated soil 13 removing hydrocarbon vapors from the soil. Apparatus 10 includes conventional moisture tension lysimeter 34 which measures the moisture content of soil within vessel 12 so that an operator or automated system, not shown, can monitor and control the moisture content of soil 13 to insure that moisture content of the soil remains at 5%–6% by weight. This, in turn, provides for optimum desorption of hydrocarbon contaminants from the soil within vessel 12 as well as promoting the biodegradation of the soil within vessel 12.

There is positioned at the top portion of vessel 12 a plurality of evenly spaced air intakes 36 which are connected to a pump 38 by a pipe 40. Pump 38, which has an operating pressure of approximately 309 psi, withdraws air including hydrocarbon vapors released from contaminated soil 13 within vessel 12 through a plurality evenly spaced air intakes 36 and pipe 40 to a treatment tank or vessel 42. Tank 42 uses potassium hydroxide (KOH) or similar compound as an absorbing agent to remove carbon dioxide from the hydrocarbon vapors. Since potassium hydroxide is used to absorb carbon dioxide from the hydrocarbon vapors, it is required that there be a periodic removal and replacement of the carbon dioxide absorbing agent within tank 42.

At this time it should be noted that biodegradation apparatus 10 may effectively treat the outgoing air from vessel 12 to render it environmentally safe without tank 42. It should also be noted that there is operatively connected to pipe 40 a vapor phase detector 44 which may, for example, be a photoionization detector for measuring the concentration of hydrocarbon vapor within the outgoing air from vessel 12.

Pump 38 next forces the hydrocarbon vapors through a pipe 46 to a vapor phase bioreactor 48 for the removal of volatile hydrocarbon contaminants or other organic vapors. The vapor phase reactor 48 may be a biofilter of granular activated carbon or granular coke, plastic or glass beads, peat or the like. In addition, the bioreactor 48 used in the preferred embodiment of the present invention may be any well known, commercially available biofilter which is highly efficient, i.e. provides for complete removal of hydrocarbon pollutants and odorous substances from the outgoing air as well as being simple in construction and operation and providing for low energy consumption (operating cost).

The outgoing air is next supplied through a pipe 50 to a conventional granular activated carbon filter 52 which absorbs any remaining hydrocarbon contaminants and then expels non-polluted air through an air exhaust pipe 54 into the atmosphere.

An operator monitoring vapor phase detector 44 will energize a pump 56, which may be any commercially available sludge pump for transporting sludge as well as water, whenever the hydrocarbon vapors flowing through pipe 40 level off to a predetermined constant value. Pump 56 will initially draw water from a reservoir, not shown, through a pipe 58, a treatment tank 60, a pipe 62 and a heater 63 to a plurality of evenly spaced high pressure injection nozzles/water jets 64 positioned at the bottom portion of vessel 12.

Treatment tank 60 has therein conventional and well known surfactants such as detergents to penetrate and help loosen nonvolatile hydrocarbon contaminants from soil particles within vessel 12. Injection nozzles 64 force water at pressures exceeding 120 psi in an upward direction within vessel 12 causing the contaminated soil 13 to churn within vessel 12 with fine particles of contaminated soil, oil and the like moving in an upward direction thereby forming a supernatant, designated generally by the reference numeral 65, at the upper portion of vessel 12. The larger particles of soil, in turn, sink to the lower portion of vessel 12.

At this time it should be noted that gravel may be placed at the bottom of vessel 12 to provide structural support for water jets 64 and air diffusers 16 at the bottom of vessel 12. In addition, it should be noted that heater 63 maintains water temperature at approximately 25°–35° C. prior to injection or reinjection of the water into the contaminated soil within vessel 12 to accelerate biodegradation and soil washing. Further, there is positioned at the end of pipe 62 a valve 67 which when opened allows water jets 64 and pipe 62 to be flushed of soils which would plug up the water jets 64 and pipes 62.

The supernatant 65 at the upper portion of vessel 12 then exits through an exit pipe 66 to a settling tank 68, which allows oil sludge and heavy nonvolatile hydrocarbon contaminants to accumulate at the bottom portion of tank 68. A pump 72 withdraws water and the remaining hydrocarbon contaminants from settling tank 68 through a connecting pipe 70 to a treatment tank 73. Treatment tank 73 has therein well known, commercially available nutrients to promote biological growth whereby the remaining hydrocarbon contaminants can be converted into environmentally-safe and non-toxic by-products. The nutrients in treatment tank 73 may be, for example, ammonium nitrate or soluble phosphates. In addition, pH buffers such as sodium hydroxide or hydrochloric acid are utilized in treatment tank to maintain a near neutral pH within treatment tank 73.

When the water within tank 73 is environmentally safe, that is all the hydrocarbon contaminants within tank 73 have been neutralized, a normally closed valve 76 is opened allowing water to be withdrawn from tank 73 through connecting pipe 74 to tank 60. The environmentally safe water from tank 73 may be recirculated through vessel 12 removing additional hydrocarbon contaminants from soil 13 until the soil within vessel 12 is rendered environmentally safe.

Removable top 14 may then be removed from vessel 12 allowing the environmentally safe soil within vessel 13 to be removed therefrom and replaced with hydrocarbon contaminated soil which may then rendered environmentally safe by utilizing biodegradation apparatus 10 of the present invention.

Biodegradation apparatus 10 includes a pipe 78 having therein a normally closed valve 80 which when opened allows oily sludge to be backflushed by pump 56 from the bottom portion of tank 68 to vessel 12 for treatment by biodegradation apparatus 10 This sludge may contain sufficient quantities of microorganisms to help promote biodegradation of new soils placed within vessel 12 for treatment. It should be noted that there is positioned at the outlet port of heater 63 a check valve 94 which prevents sludge from flowing back through heater 63.

Biodegradation apparatus 10 also includes a drain pipe 90 which includes a normally closed valve 92 which when opened allows water to be drained from vessel 12 into the surrounding soil. Valve 92, in turn, is utilized only when the water within vessel 12 is rendered environmentally safe.

Biodegradation apparatus 10 also includes a drain pipe 98 which includes a normally closed valve 98 which when opened allows water to be drained from tank 60 into the surrounding soil. Valve 96, in turn, is utilized only when the water within tank 60 is rendered environmentally safe.

At this time it should be noted that while only biodegradation of hydrocarbon contaminants by utilizing the apparatus of the present invention is described, biodegradation apparatus 10 may be used to remove any biodegradable volatile organic compounds to render soils environmentally safe.

From the foregoing, it may readily be seen that the subject invention comprises a new, unique and exceeding useful method and apparatus for the biodegradation of volatile organic compounds such as hydrocarbon contaminants within soils which constitutes a considerable improvement over the known prior art. Obviously, many modifications and variations of the present invention are possible in light of the above teachings. It is therefore to be understood that within the scope of the appended claims the invention may be practiced otherwise than as specifically described.

What is claimed is:

1. An apparatus for the continuous treatment of soils contaminated with volatile and nonvolatile hydrocarbon contaminants, said apparatus biodegrading said volatile and nonvolatile hydrocarbon contaminants thereby rendering said soils environmentally safe, said apparatus comprising:

an enclosed primary vessel having a removable top and a bottom, said enclosed primary vessel being adapted to receive and hold said contaminated soils so as to allow said hydrocarbon contaminants to be removed from the soils within said enclosed vessel;

a plurality of evenly spaced air diffusers positioned at the bottom of said enclosed vessel;

first pumping means for providing moist air to said enclosed vessel and for forcing said moist air through said air diffusers in an upward direction through said enclosed vessel so as to remove said volatile hydrocarbon contaminants from said soils;

a plurality of evenly spaced air intakes positioned at the top of said enclosed vessel;

second pumping means for withdrawing said moist air including said volatile hydrocarbon contaminants from said enclosed vessel through said air intakes;

a vapor phase bioreactor connected to said second pumping means for removing said volatile hydrocarbon contaminants from said moist air withdrawn from said enclosed vessel;

a granular activated carbon filter connected to said vapor phase bioreactor for absorbing any remaining hydrocarbon contaminants from said moist air withdrawn from said enclosed vessel;

said granular activated carbon filter having an air exhaust pipe, said granular activated carbon filter expelling environmentally safe non-polluted air through said air exhaust pipe;

a plurality of evenly spaced water jets positioned at the bottom of said enclosed vessel;

third pumping means connected to said enclosed vessel for providing water to said enclosed vessel and for forcing water provided to said enclosed vessel through said water jets in an upward direction through said enclosed vessel so as to remove said nonvolatile hydrocarbon contaminants from said soils;

first treatment tank means connected to said third pumping means for storing water to be provided to said enclosed vessel, said first treatment tank means having therein surfactants, said surfactants being added to the water stored within said first treatment tank means to allow the water provided to said enclosed vessel to penetrate and loosen said nonvolatile hydrocarbon contaminants from said soils, the water having said nonvolatile hydrocarbon contaminants added thereto forming a supernatant, said supernatant being formed within said vessel above said contaminanted soils and below said evenly spaced air intakes, said supernatant including oil sludge;

second treatment tank means connected to said enclosed vessel;

fourth pumping means connected to said second treatment tank means for withdrawing said supernatant from said enclosed vessel and providing said supernatant to said second treatment tank means, said oil sludge and heavy nonvolatile hydrocarbon contaminants within said supernatant settling to the bottom of said second treatment tank means;

third treatment tank means connected to said fourth pumping means, said third treatment tank means having nutrients to effect biological growth of microorganisms within said nonvolatile hydrocarbon contaminants such that the remainder of said nonvolatile hydrocarbon contaminants are degraded and converted into a non-toxic condition;

said third treatment tank means being connected to said first treatment tank means so as to return water treated within said second and third treatment tank means to said first treatment tank means.

2. The biodegrading apparatus of claim 1 further comprising fourth treatment tank means connected to the said second pumping means and said vapor phase bioreactor for removing carbon dioxide from said moist air withdrawn from said enclosed vessel.

3. The biodegrading apparatus of claim 1 wherein said vapor phase bioreactor comprises a biofilter of activated granular carbon.

4. The biodegrading apparatus of claim 1 wherein said vapor phase bioreactor comprises a biofilter of granular coke.

5. The biodegrading apparatus of claim 1 wherein said vapor phase bioreactor comprises a biofilter of glass beads.

6. The biodegrading apparatus of claim 1 wherein said vapor phase bioreactor comprises a biofilter of peat.

7. The biodegrading apparatus of claim 1 further comprising a vapor phase detector effectively connected to said enclosed vessel for measuring the concentration of hydrocarbon vapor within the air being withdrawn from said enclosed vessel.

8. The biodegrading apparatus of claim 1 further comprising a moisture tension lysimeter operatively connected to said enclosed vessel for measuring the moisture content of said soils within said enclosed vessel.

9. The biodegrading apparatus of claim 1 further comprising a normally closed valve connected between said first and third treatment tank means.

10. The biodegrading apparatus of claim 1 further comprising a return pipe connected between the bottom of said second treatment tank means and said third pumping means, said return pipe having therein a normally closed valve which when opened allows oil sludge to be backflushed by said third pumping means from the bottom of said second treatment tank means to said enclosed vessel.

11. The biodegrading apparatus of claim 1 further comprising a heater connected between said first treatment tank means and said third pumping means and a check valve connected between said heater and said third pumping means.

12. The biodegrading apparatus of claim 1 wherein said enclosed vessel is fabricated from a nonporous material.

13. The biodegrading apparatus of claim 12 wherein said nonporous material is concrete.

14. The biodegrading apparatus of claim 1 wherein said first pumping means comprises:

a pump having an inlet port and an outlet port, the outlet port of said pump being connected to said air diffusers within said enclosed vessel;

a humidifier having an inlet port and an outlet port;

a diverter valve having an inlet port and first and second outlet ports, the first outlet port of said diverter valve being connected to the inlet port of said humidifier;

a check valve being an inlet port connected to the outlet port of said humidifier and an outlet port connected to the inlet port of said pump; and a bypass pipe connected between the second outlet port of said diverter valve and the inlet port of said pump.

15. The biodegrading apparatus of claim 14 further comprising a heater having an inlet port adapted to receive air and an outlet port connected to the inlet port of said diverter valve.

* * * * *